US007611890B2

(12) United States Patent
Frisch et al.

(10) Patent No.: US 7,611,890 B2
(45) Date of Patent: Nov. 3, 2009

(54) SYSTEM AND METHOD FOR SEPARATING BIOMASS FROM MEDIA IN A FLUIDIZED BED REACTOR

(76) Inventors: Samuel Frisch, 57 Jeanin Ct., Manalapan, NJ (US) 07726; Robert E. Loudon, 134 Maxim Rd., Howell, NJ (US) 07731

( * ) Notice: Subject to any disclaimer, the term of this patent is extended or adjusted under 35 U.S.C. 154(b) by 562 days.

(21) Appl. No.: 10/877,338

(22) Filed: Jun. 25, 2004

(65) Prior Publication Data

US 2005/0287659 A1 Dec. 29, 2005

(51) Int. Cl.
*C12M 1/00* (2006.01)
*C12M 3/00* (2006.01)

(52) U.S. Cl. .................................................. 435/289.1

(58) Field of Classification Search .............. 435/289.1, 435/295.2, 308.2, 308.1

See application file for complete search history.

(56) References Cited

U.S. PATENT DOCUMENTS 2,083,348 A * 6/1937 Scholler et al. .......... 435/295.2
2,146,326 A 2/1939 Bergins et al.
3,705,082 A 12/1972 Hondermarck et al.
3,717,552 A 2/1973 Hondermarch et al.
3,855,120 A 12/1974 Garbu
3,910,826 A 10/1975 Kataoka
4,026,674 A 5/1977 McDonald
4,177,144 A * 12/1979 Hickey et al. ................. 210/86
4,250,033 A 2/1981 Hickey et al.
4,357,424 A 11/1982 Bu'Lock
4,545,909 A 10/1985 Atkinson et al.
4,561,974 A 12/1985 Bernard et al.
4,589,927 A 5/1986 Allen et al.
4,681,685 A 7/1987 Sutton et al.
4,707,252 A 11/1987 Durot et al.
4,708,936 A 11/1987 Kulla et al.
4,882,068 A 11/1989 Blom
4,892,818 A 1/1990 Ramp
4,904,600 A 2/1990 Ramp
4,954,259 A 9/1990 Elmaleh et al.
4,959,084 A 9/1990 Wolverton et al.
5,166,072 A 11/1992 Krauling et al.
5,173,194 A 12/1992 Hering, Jr.
5,260,216 A 11/1993 Hirose
5,277,829 A 1/1994 Ward
5,316,945 A 5/1994 Minuth
5,342,781 A 8/1994 Su
5,454,938 A * 10/1995 Doyle et al. ................ 210/106

(Continued)

*Primary Examiner*—Walter D Griffin
*Assistant Examiner*—Shanta G Doe
(74) *Attorney, Agent, or Firm*—RatnerPrestia

(57) ABSTRACT

A system is provided for separating biomass from media in a fluidized bed reactor containing an aqueous suspension of biomass and media. A lift, configured to extend within the reactor, has an inlet for receiving aqueous suspension and an outlet spaced from the inlet for delivering the aqueous suspension from the lift. A shield is disposed about the lift. The system further includes a biomass separator body, including an inner member disposed about the shield and an outer member. Three annular passageways are defined between the lift, the shield, the inner member, and the outer member, and are positioned to receive aqueous suspension from each other. A barrier extends between the inner member and the outer member at an end portion of the third annular passageway. The barrier of the biomass separator body is configured to direct biomass from the third annular passageway toward an excess biomass discharge.

22 Claims, 5 Drawing Sheets

U.S. PATENT DOCUMENTS

| | | | |
|---|---|---|---|
| 5,487,829 A | 1/1996 | Safferman et al. | |
| 5,494,574 A | 2/1996 | Unterman et al. | |
| 5,573,663 A | 11/1996 | Junius et al. | |
| 5,573,671 A | 11/1996 | Klein | |
| 5,750,028 A | 5/1998 | Frisch | |
| 5,788,842 A | 8/1998 | Frisch | |
| 5,985,149 A | 11/1999 | Raetz et al. | |
| 2003/0036191 A1* | 2/2003 | Frisch | 435/295.2 |

* cited by examiner

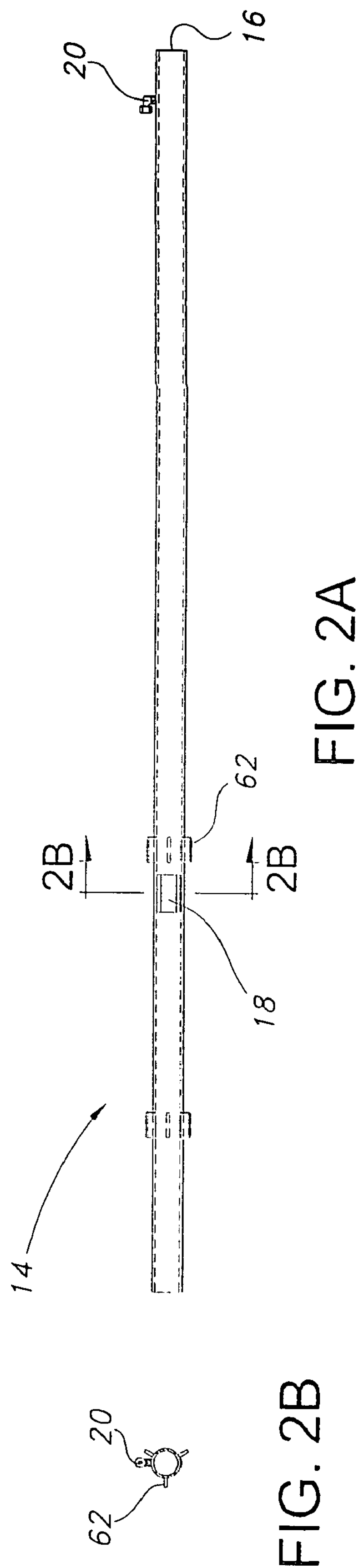
FIG. 2A
FIG. 2B
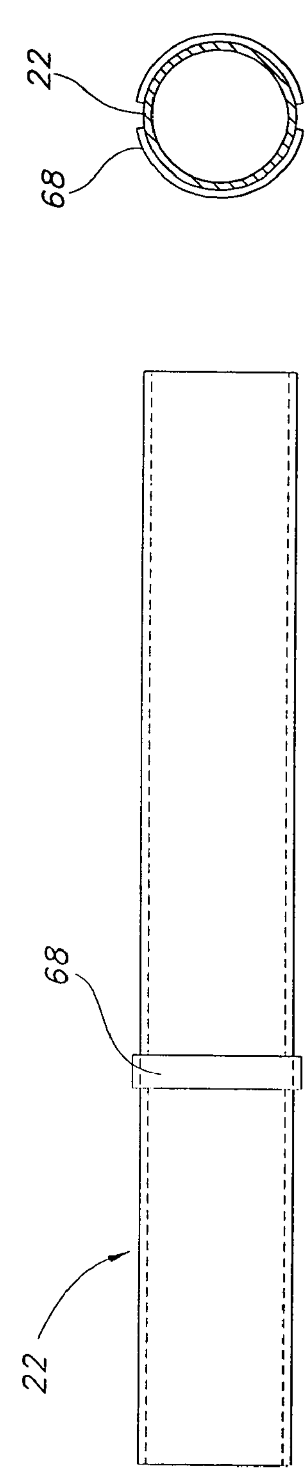
FIG. 3B
FIG. 3A

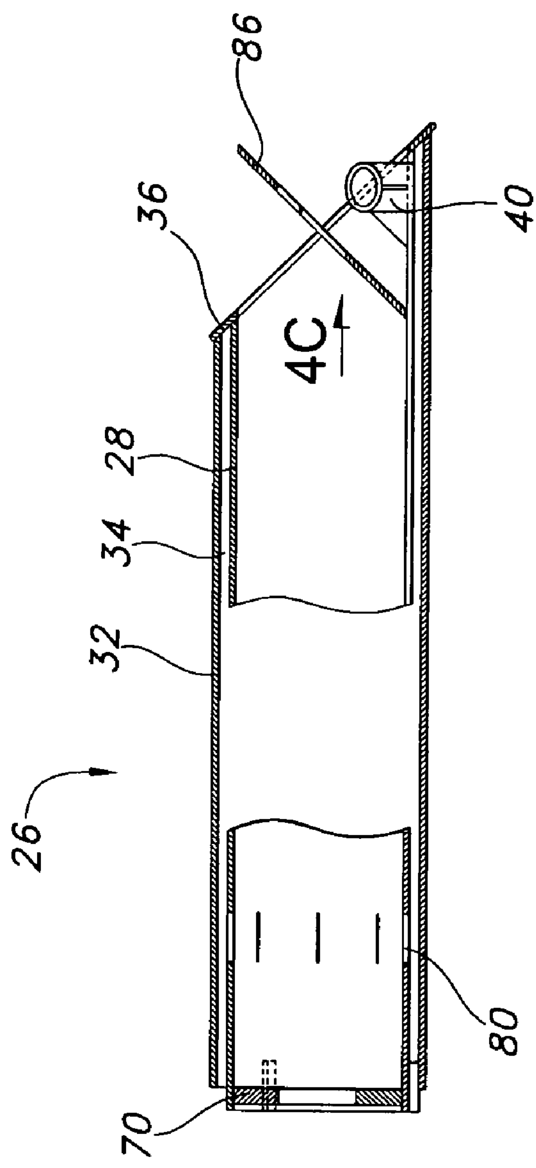
FIG. 4A
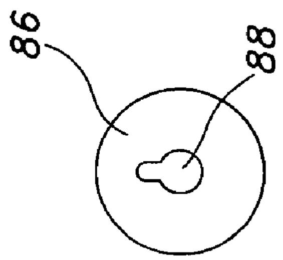
FIG. 4C
FIG. 4B

SYSTEM AND METHOD FOR SEPARATING BIOMASS FROM MEDIA IN A FLUIDIZED BED REACTOR

FIELD OF THE INVENTION

The present invention relates to bioreactors, and more specifically, to the control of biomass growth on suspended media within fluidized-bed bioreactors.

BACKGROUND OF THE INVENTION

Biological reactors find increasing use in many areas of industry, including waste treatment plants. Efforts to protect the environment include advanced biological treatment of wastewater through the use of biological reactors, and in particular, fluidized-bed bioreactors. It is the activity of biologically active materials (or "biomass") within the biological reactor that degrades contaminants in the influent to effect a filtration process. As the biomass treats, through enzymatic reaction, these contaminants, the biomass grows through reproduction within the system. Typically, this activity occurs within a treatment vessel which contains media or other substrate material or carriers on which the biomass attaches and grows as contaminants are consumed. Typical media would include plastic beads, resin beads, sand, activated carbon, or ion exchange resins, among other carriers.

Conventional fluidized-bed bioreactors, such as well-mixed suspended carrier reactors (SCRs), suffer from operational drawbacks in that the media or carriers of the fluidized bed may be subject to excessive buildup of biomass and precipitates, thereby causing compromised flow distribution, excessive media and/or biomass carryover, crusting, increased clogging of filters, and the like. If not properly limited, biomass and precipitate buildup is detrimental to system performance. Uncontrolled biomass film growth in a fluidized bed biological reactor can also result in an undesirable loss of media.

Media bed expansion can, under certain circumstances, be limited by the application of shear at the top of the media bed, but the success of such a control strategy depends upon whether excess biomass and suspended solids can be transported to the top of the fluidized bed. More specifically, it is recognized that such transportation of excess biomass and suspended solids toward the top of the bed is promoted by several dominant mechanisms. For example, media grains that are coated with thicker layers of biomass tend to have an overall particle density that is less than the average particle density within the fluidized bed. Those particles, therefore, are transported to the top of the fluidized bed by virtue of upward moving fluid flow as well as the reduced particle density. This upward movement results in some shear forces acting on biomass-covered particles which does separate some biomass from its supportive media.

Though media bed expansion can therefore be reduced by the application of shear, there remains a need in the industry for an improved system for removing accumulated biomass from a slurry of a fluidized-bed bioreactor to inhibit uncontrolled biomass growth and precipitate accumulation.

SUMMARY OF THE INVENTION

According to one aspect of this invention, a system is provided for separating biomass from media in a fluidized bed reactor (FBR) containing an aqueous suspension of biomass and media. The system includes a lift configured to extend within the reactor. The lift has an inlet for receiving aqueous suspension and an outlet spaced from the inlet for delivering the aqueous suspension from the lift. A gas inlet is positioned to feed gas into the lift for urging the aqueous suspension toward the outlet of the lift. A shield is disposed about the lift and defines a first annular passageway between the shield and the lift. The first annular passageway is positioned to receive aqueous suspension from the outlet of the lift. The system further includes a biomass separator body. The biomass separator includes an inner member disposed about the shield and a second annular passageway defined between the inner member of the biomass separator body and the shield. The second annular passageway is positioned to receive aqueous suspension from the first annular passageway. The biomass separator further includes an outer member, wherein a third annular passageway is defined between the inner member and the outer member. The third annular passageway is positioned to receive aqueous suspension from the second annular passageway. A barrier extends between the inner member and the outer member at an end portion of the third annular passageway. An excess biomass discharge is in fluid communication with the third annular passageway. The barrier of the biomass separator body is configured to direct biomass from the third annular passageway toward the excess biomass discharge.

According to another aspect of this invention, a fluidized bed reactor includes a reactor vessel configured to contain an aqueous suspension of biomass and media. The fluidized bed reactor also includes a lift; a gas inlet; a shield; and a biomass separator body including an inner member, an outer member, a barrier, and an excess biomass discharge. According to yet another aspect of this invention, a method is provided for separating biomass from media in a fluidized bed reactor containing an aqueous suspension of biomass and media. Gas is fed into a lift extending within the fluidized bed reactor, thereby urging aqueous suspension from an inlet of the lift toward an outlet of the lift. Aqueous suspension is directed from the outlet of the lift to a first annular passageway. Aqueous suspension flows from the first annular passageway to a second annular passageway, thereby separating media from biomass. Aqueous suspension is redirected from the second annular passageway to a third annular passageway. Finally, biomass is discharged from the third annular passageway.

BRIEF DESCRIPTION OF THE DRAWINGS

FIG. 2A is a detailed side view of an exemplary embodiment of a lift of the system illustrated in FIG. 1A;

FIG. 2B is an end view of the lift illustrated in FIG. 2A;

FIG. 3A is a detailed side view of an exemplary embodiment of a shield of the system illustrated in FIG. 1A;

FIG. 3B is an end view of the shield illustrated in FIG. 3A;

FIG. 4A is a cross-sectional side view of an exemplary embodiment of the biomass separator body of the system illustrated in FIG. 1A;

FIG. 4B is an end view of the biomass separator body illustrated in FIG. 4A;

FIG. 4C is a plan view of an embodiment of a deflector of the biomass separator body illustrated in FIG. 4A;

DETAILED DESCRIPTION OF THE INVENTION

Figure 1A:
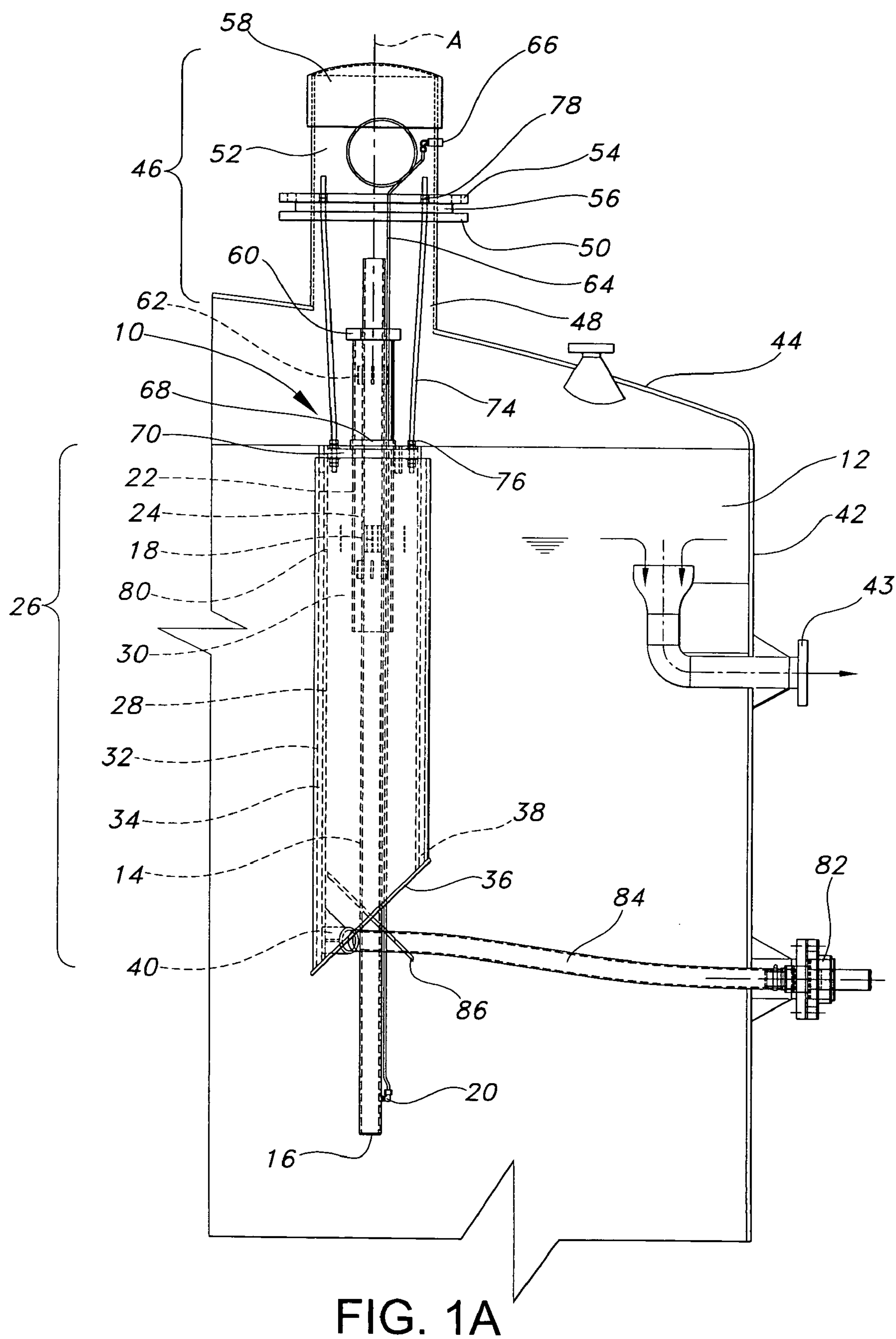
FIG. 1A is a partial side view of an exemplary embodiment of a system for separating biomass from media in a fluidized bed reactor, illustrating an excess biomass discharge positioned on an inner member of a biomass separator body in accordance with aspects of the present invention.

Although the invention is illustrated and described herein with reference to specific embodiments, the invention is not intended to be limited to the details shown. Rather, various modifications may be made in the details within the scope and range of equivalents of the claims and without departing from the invention.

Referring generally to FIGS. 1A-5B, a system 10 is provided for separating biomass from media in a fluidized bed reactor 12 containing an aqueous suspension of biomass and media. The system 10 includes a lift 14 configured to extend within the reactor 12. The lift 14 has an inlet 16 for receiving aqueous suspension and an outlet 18 spaced from the inlet 16 for delivering the aqueous suspension from the lift 14. A gas inlet 20 is positioned to feed gas into the lift 14 for urging the aqueous suspension toward the outlet 18 of the lift 14. A shield 22 is disposed about the lift 14 and defines a first annular passageway 24 between the shield 22 and the lift 14. The first annular passageway 24 is positioned to receive aqueous suspension from the outlet 18 of the lift 14. The system 10 further includes a biomass separator body 26. The biomass separator 26 includes an inner member 28 disposed about the shield 22 and a second annular passageway 30 defined between the inner member 28 of the biomass separator body 26 and the shield 22. The second annular passageway 30 is positioned to receive aqueous suspension from the first annular passageway 24. The biomass separator 26 further includes an outer member 32, wherein a third annular passageway 34 is defined between the inner member 28 and the outer member 32. The third annular passageway 34 is positioned to receive aqueous suspension from the second annular passageway 30. A barrier 36 extends between the inner member 28 and the outer member 32 at an end portion 38 of the third annular passageway 34. An excess biomass discharge 40 is in fluid communication with the third annular passageway 34. The barrier 36 of the biomass separator body 26 is configured to direct biomass from the third annular passageway 34 toward the excess biomass discharge 40.

In use, gas is fed into the lift 14 extending within the fluidized bed reactor 12, thereby urging aqueous suspension from the inlet 16 of the lift 14 toward the outlet 18 of the lift 14. Aqueous suspension is directed from the outlet 18 of the lift 14 to the first annular passageway 24. Aqueous suspension flows from the first annular passageway 24 to the second annular passageway 30, thereby separating media from biomass. Aqueous suspension is redirected from the second annular passageway 30 to the third annular passageway 34. Finally, biomass is discharged from the third annular passageway 34.

Figure 1B:
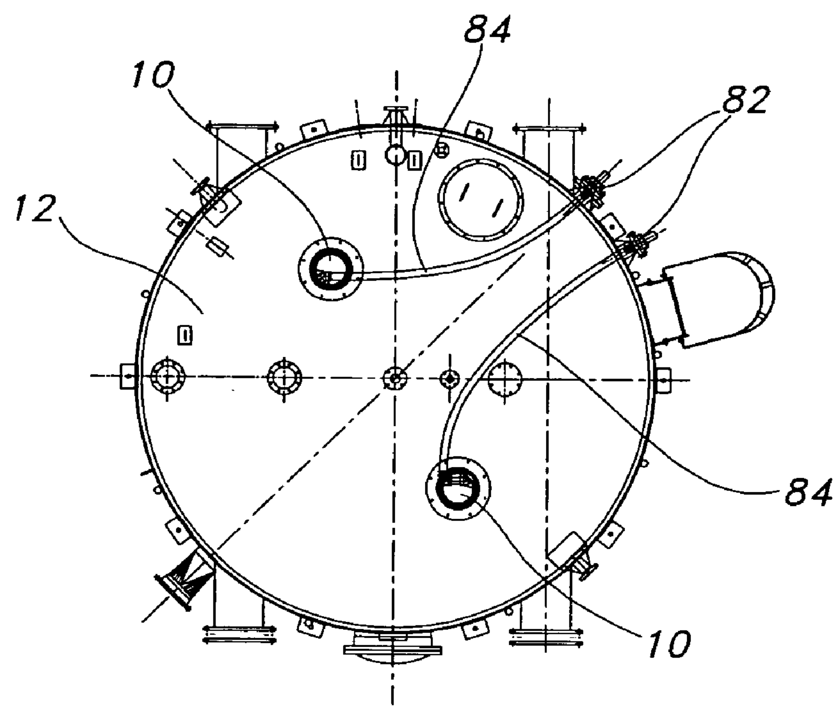
FIG. 1B is a plan view of the system illustrated in FIG. 1A.

Referring specifically to FIGS. 1A and 1B, there is shown a system 10 for separating biomass from media in a fluidized bed reactor 12 containing an aqueous suspension of biomass and media. The general structure of the fluidized bed reactor 12 includes a reactor vessel 42 covered by a dome 44. A cap assembly 46 is integrated into the dome 44. The cap assembly 46 includes a vessel pipe 48 with a vessel flange 50, and a cap pipe 52 with a cap flange 54. A spacer plate 56 is sandwiched between the cap flange 54 and the vessel flange 50 along with a gasket (not shown) on each side of the spacer plate 56 to help maintain a seal between the cap pipe 52 and the vessel pipe 48. During normal operation, a cap 58 is sealed to the top of the cap pipe 52 to help maintain an anaerobic bioreactor system. In other words, the sealed cap 58 helps to ensure that the fluidized bed reactor 12 remains free of oxygen.

The level of the aqueous solution within the reactor vessel 42 is represented symbolically in FIG. 1A slightly above an overflow outlet 43. The level of the aqueous solution is set by a vessel overflow connection (not shown).

The system 10 is generally oriented along longitudinal axis A, and includes a lift 14 configured to extend within the reactor 12. Attached around the circumference of the lift 14 is a riser clamp 60 that rests on top of a shield 22 (described below), thereby supporting the lift 14 in position with respect to the shield 22. The lift 14 includes spacers 62 located along its outer circumference to help center the lift 14 within the shield 22 (described below). The lift 14 has an inlet 16 for receiving aqueous suspension and outlets 18 (one shown) spaced from the inlet 16 for delivering the aqueous suspension from the lift 14.

A gas inlet 20 is positioned to feed gas into the lift 14, proximal to or at a lower end portion of the lift 14, for urging the aqueous suspension toward the outlets 18 of the lift 14. The gas inlet 20 is fed by a gas line 64 which is supplied with gas at the gas port 66. The gas provided to gas inlet 20 is optionally air or other available gas. As the gas enters the lift 14, it rises by buoyancy toward the outlets 18 of the lift 14. By this action, the gas acts as a motive for the movement of aqueous suspension into and through the lift 14 and toward the outlets 18. Gas bubbles may optionally collect in the lift 14 to form "slugs" of motive gas rising within the lift.

The shield 22 is disposed about the lift 14 via the riser clamp 60. More specifically, the riser clamp 60 acts as a collar around the lift 14 that rests on top of the shield 22 to support the lift 14 with respect to the shield 22. As explained above, the lift 14 includes spacers 62 located along its outer circumference to help center the lift 14 within the shield 22.

A first annular passageway 24 is defined between the shield 22 and the lift 14. The spacers 62 help to ensure that the width of the first annular passageway 24 is consistent throughout, though the width of the first annular passageway 24 can optionally vary along its length or about its circumference. The first annular passageway 24 is positioned to receive aqueous suspension from the outlets 18 of the lift 14. More specifically, the first annular passageway 24 receives aqueous suspension from the lift 14 via outlets 18 formed in the lift 14. The shield 22 further includes a collar 68 around the circumference of the shield 22 that rests on a support plate 70 (described below), thereby supporting the shield 22 in position within the reactor vessel 42.

The system 10 further includes a biomass separator body 26 disposed about the shield 22. The support plate 70 located at the top portion of the biomass separator body 26 includes a round hole 72 in its center (illustrated in FIG. 4B) to accommodate the shield 22. As explained above, the collar 68 of the shield 22 rests on the support plate 70 to support the shield 22.

The biomass separator body 26 is suspended within the reactor vessel 42 by three threaded rods 74 (two are shown). More specifically, the support plate 70 located at the top portion of the biomass separator body 26 is fixedly secured to the threaded rods 74 via fastener assemblies 76. Each threaded rod 74 extends upwardly from the support plate 70 of the biomass separator body 26 through the dome 44 of the reactor vessel 42, through the vessel flange 50, through the spacer plate 56, and through the cap flange 54, and is moveably secured at the cap flange 54 via respective adjustment nuts 78.

The elevation of the biomass separator body 26 within the reactor vessel 42 is adjustable through manipulation of the adjustment nuts 78. More specifically, when the adjustment nuts 78 are rotated in one direction, the respective threaded rods 74 travel towards the cap 58 causing the biomass separator body 26 to rise. When the adjustment nuts 78 are rotated in the opposite direction, the respective threaded rods 74 travel away from the cap 58, causing the biomass separator body 26 to lower. Changing the elevation of the separator body 26 relative to the level of aqueous suspension in the vessel 42 affects the flow rate of the aqueous suspension, as will be described in greater detail below.

The biomass separator body 26 includes an inner member 28 disposed about the shield 22 and a second annular passageway 30 is defined between the inner member 28 of the biomass separator body 26 and the shield 22. The second annular passageway 30 is positioned to receive aqueous suspension from the first annular passageway 24. More specifically, the second annular passageway 30 receives aqueous suspension from the first annular passageway 24 by means of the flow of aqueous suspension from the lower end of the shield 22 and the redirection of at least a portion of the flow upwardly into the space between the inner member 28 and the shield 22.

The biomass separator 26 further includes an outer member 32, wherein a third annular passageway 34 is defined between the inner member 28 and the outer member 32. The inner member 28 includes apertures 80 through which the third annular passageway 34 receives aqueous suspension from the second annular passageway 30. More specifically, aqueous suspension flows upwardly in the second annular passageway 30, from the second annular passageway 30 to the third annular passageway 34 through the apertures 80, and downwardly through the third annular passageway 34.

The reactor vessel 42 contains an aqueous suspension of biomass and media, and the system 10 separates the biomass from the media. As mentioned above, changing the elevation of the separator body 26 relative to the level of aqueous suspension in the vessel 42 affects the flow rate of the aqueous suspension from the second annular passageway 30 to the third annular passageway 34 through the apertures 80. Excessive flow may cause media carryover into the third annular passageway 34. Insufficient flow may not remove enough biomass from the media. A typical flow rate with carbon utilized as the media is about 5-10 gallons per minute, and a typical flow rate with sand utilized as the media is about 5-20 gallons per minute. Other flow rates and media materials are contemplated as well.

A barrier 36 extends between the inner member 28 and the outer member 32 at an end portion 38 of the third annular passageway 34. An excess biomass discharge 40, positioned on the inner member 28, is in fluid communication with the third annular passageway 34. The barrier 36 of the biomass separator body 26 is configured (e.g., positioned and oriented) to direct biomass from the third annular passageway 34 toward the excess biomass discharge 40. More specifically, in the embodiment illustrated in FIG. 1A, the barrier 36 is downwardly sloped to direct biomass by gravity toward the discharge 40, preferably in such a way as to reduce buildup of biomass within the third annular passageway 34.

The excess biomass discharge 40 discharges excess biomass from the third annular passageway 34 through a vessel biomass discharge nozzle assembly 82 (located external to the reactor vessel 42) via a discharge hose 84. The excess biomass is thereby removed from the FBR 12 for disposal or further treatment.

A deflector 86 having a hole 88 (illustrated in FIG. 4C) to accommodate the lift 14 is positioned to deflect media exiting the inner member 28. More specifically, the deflector 86 is angled with respect to longitudinal axis A of the inner member 28 to direct media away from the inlet 16 of the lift 14. Thus, the recirculation of separated media through the lift is reduced by reducing the concentration of separated media at the inlet 16 of the lift 14. More specifically, media is optionally more dense than the aqueous solution and therefore flows downwardly by action of gravity. And as media flows downwardly through the annular space between the lift 14 and the inner member 28, it is washed by countercurrent flow of aqueous solution that may enter into the base of inner member 28. As the media exits the inner member 28, it is directed radially or sidewardly away from the inlet 16 by deflector 86.

Furthermore, the deflector 86 is oriented to promote movement of aqueous suspension in the fluidized bed reactor 12. More specifically, the sideward redirection of the media causes movement of the aqueous solution within the vessel. For example, in an embodiment having multiple biomass separators (such as those illustrated in FIGS. 1B and 5B), the orientations of the deflectors of the respective separators can be coordinated to cooperate in the mixing of aqueous solution in the FBR. If for example the deflectors are oriented toward opposite directions, each parallel to the wall of the FBR, then the deflectors will encourage a swirling of the contents of the FBR. Other orientations are contemplated as well. Such movement of the aqueous solution by orientation of one or more barriers encourages advantageous mixing in the FBR.

The reactor vessel 42 and the dome 44 may be made from stainless steel, coated steel, fiberglass, or any other non-reactive material that provides the necessary structure. The cap assembly 46 components are typically made from polyvinyl chloride material, but may be made from alternative materials. The biomass separator body 26 may be made from stainless steel, polyvinyl chloride material, or any other suitable material.

FIGS. 2A and 2B illustrate the lift 14 in greater detail. As explained above, the lift 14 includes spacers 62 located along its outer circumference to center the lift 14 within the shield 22 (as illustrated in FIG. 1A). Typically the lift will include three spacers 62 equally spaced around its circumference in two locations, as shown in FIG. 2B. However, it is contemplated that any number of spacers may be utilized that achieves the desired centering feature. The lift 14 has an inlet 16 for receiving aqueous suspension and outlets 18 (one viewed in FIG. 2A, the other one diametrically opposed) spaced from the inlet 16 for delivering the aqueous suspension from the lift 14. A gas inlet 20 is positioned to feed gas into the lift 14 for urging the aqueous suspension toward the outlet 18 of the lift 14.

The lift 14 is optionally formed from pipe or tubing, though other forms are contemplated as well. Also, although the cross-sectional shape of lift 14 as illustrated is round, it is optionally any geometric shape.

FIGS. 3A and 3B illustrate the shield 22 in greater detail. As explained above, the shield 22 includes a collar 68 (shown in two pieces in FIG. 3B) around the circumference of the shield 22 that rests on the support plate 70 (as illustrated in FIG. 1A). The shield 22 is optionally formed from pipe or tubing, though other forms are contemplated as well. Also, as for the lift 14, although the cross-sectional shape of shield 22 as illustrated is round, it is optionally any geometric shape.

FIGS. 4A-4C illustrate the biomass separator body 26 in greater detail. The biomass separator body 26 includes an inner member 28 disposed about the shield 22 (as illustrated in FIG. 1A) and an outer member 32, wherein a third annular passageway 34 is defined between the inner member 28 and the outer member 32. The inner member 28 includes apertures 80 through which the third annular passageway 24 receives aqueous suspension from the second annular passageway 30 (illustrated in FIG. 1A). The apertures 80 are slotted openings, typically eight of which are spaced equally around the circumference of the inner member 28. However, it is contemplated that any shape and any number of apertures 80 may be utilized that achieves the desired flow feature.

The support plate 70 (best seen in FIG. 4B) located at the top portion of the biomass separator body 26 includes a round hole 72 in its center to accommodate the shield 22 (as illustrated in FIG. 1A). The biomass separator body 26 includes shims 90 between the inner member 28 and the outer member 32 to help center the inner member 28 within the outer member 32. The shims 90 also help to ensure that the width of the third annular passageway 34 is consistent throughout. Typically, three shims 90 are spaced equally around the circumference of the third annular passageway 34. However, it is contemplated that any number of shims 90 may be utilized that achieves the desired centering and spacing features.

As explained above, the hole 88 of the deflector 86 (best seen in FIG. 4C) accommodates the lift 14 (as illustrated in FIG. 1A). The extended portion of the hole 88 accommodates the gas line 64 through which gas is delivered to the lift 14. Accordingly, an assembly of the lift 14 and gas line 64 can be inserted through the hole 88 of the deflector 86 after the deflector 86 is assembled with the remainder of the separator body.

FIG. 4A illustrates that, as explained above, the barrier 36 extends between the inner member 28 and the outer member 32 at the end portion 38 of the third annular passageway 34. Furthermore, the excess biomass discharge 40 is positioned on the inner member 28, and is in fluid communication with the third annular passageway 34. By positioning the discharge 40 on the inner member 28 (as opposed to the outer member 32), the structure of the discharge 40 (e.g., spud or nipple or coupling) does not enlarge the profile of the biomass separator body 26. Accordingly, the discharge 40 will not interfere with the introduction of the separator body 26 into the FBR 12 through the opening of the vessel pipe 48.

In general, prior to use, the biomass separator body 26 is positioned at a default elevation within the reactor vessel 42 utilizing the adjustment nuts 78. Adjustment nuts 78 may be manipulated independently to achieve leveling of the biomass separator body 26. Typically the default elevation is maintained throughout the life of the system 10. However, it is contemplated that the elevation of the biomass separator body 26 within the reactor vessel 42 may be adjusted, as necessary, utilizing the adjustment nuts 78. Such adjustments would require removal of the cap 58 to gain access to the system.

The shield 22 is lowered into the biomass separator body 26 through the hole 72 of the support plate 70 until the collar 68 of the shield 22 abuts against the support plate 70. A riser clamp 60 is attached to the lift 14 at a predetermined location, and then the lift 14 is lowered into the shield 22 until the riser clamp 60 abuts against the top of the shield 22. Typically the predetermined location of the riser clamp 60 attachment to the lift 14 maintains the lift 14 at an elevation with respect to the shield 22 throughout the life of the system 10. However, it is contemplated that the elevation of the lift 14 may be adjusted, as necessary, depending upon where the riser clamp 60 is attached to the lift 14. In other words, to raise the elevation of the lift 14, the riser clamp 60 would be attached at a lower location on the lift 14. Conversely, to lower the elevation of the lift 14, the riser clamp 60 would be attached at a higher location on the lift 14. Such adjustments would require removal of the cap 58 to gain access to the system 10.

Generally, the outlets 18 of the lift 14 are positioned near the FBR 12 overflow elevation. By adjusting the elevation of the lift 14, along with its associated gas line 64 and gas inlet 20, the flow rate and magnitude of shear of the aqueous suspension are controlled. More specifically, raising the lift 14 reduces the flow of aqueous suspension through the lift 14 and causes longer residence time of the aqueous suspension in the lift 14, resulting in greater shear.

The reactor vessel 42 contains an aqueous suspension of biomass and media. The media may consist of sand or plastic, and the biomass, which is lighter than the media, grows on the media. The system 10 separates the biomass from the media, thereby cleaning the media so that it may eventually be recycled.

During operation, gas is fed into the lift 14 extending within the fluidized bed reactor 12. More specifically, the gas inlet 20 is fed by a gas line 64 which is supplied with gas at the gas port 66. As bubbles of gas rise up through the lift 14, aqueous suspension from the reactor vessel 42 is urged through the inlet 16 of the lift 14 toward the outlets 18 of the lift 14. Aqueous suspension is directed from the outlets 18 of the lift 14 to the first annular passageway 24. The aqueous suspension travels down the first annular passageway 24 until it is no longer constrained by the shield 22.

Aqueous suspension then flows from the first annular passageway 24 to the second annular passageway 30, thereby separating media from biomass. In other words, most of the heavier media tends to sink down within the inner member 28 toward the deflector 86, while the most of the lighter biomass tends to float up the second annular passageway 30 toward the apertures 80 of the inner member 28. As explained above, the deflector 86 is positioned to deflect media exiting the inner member 28. More specifically, the deflector 86 is angled with respect to longitudinal axis A of the inner member 28 to direct media away from the inlet 16 of the lift 14. Furthermore, the deflector 86 is oriented to promote movement of aqueous suspension in the fluidized bed reactor 12.

Aqueous suspension, containing mostly biomass, is redirected from the second annular passageway 30 to the third annular passageway 34. More specifically, the third annular passageway 34 receives aqueous suspension from the second annular passageway 30 through the apertures 80 of the inner member 28.

The aqueous suspension, containing mostly biomass, then sinks toward the end portion 38 of the third annular passageway 34. As explained above, the excess biomass discharge 40 is positioned on the inner member 28, and is in fluid communication with the third annular passageway 34. The barrier 36 of the biomass separator body 26 is configured to direct biomass from the third annular passageway 34 toward the excess biomass discharge 40. More specifically, the barrier 36 is downwardly sloped (as illustrated in FIG. 1A) to reduce buildup of biomass within the third annular passageway 34. The excess biomass discharge 40 discharges excess biomass from the third annular passageway 34 through a vessel biomass discharge nozzle assembly 82 (located external to the reactor vessel 42) via a discharge hose 84 (as illustrated in FIG. 1A).

Due to the improved design of the system 10, including the downwardly sloped orientation of the barrier 36 to reduce buildup of biomass within the third annular passageway 34, the system 10 is virtually self-cleaning. However, in the unlikely event that biomass does build up within the third annular passageway 34, the top portion of the third annular passageway 34 is open and located above water level for ease of cleaning. Such cleaning would require removal of the cap 58 to gain access to the system 10.

Figure 5B:
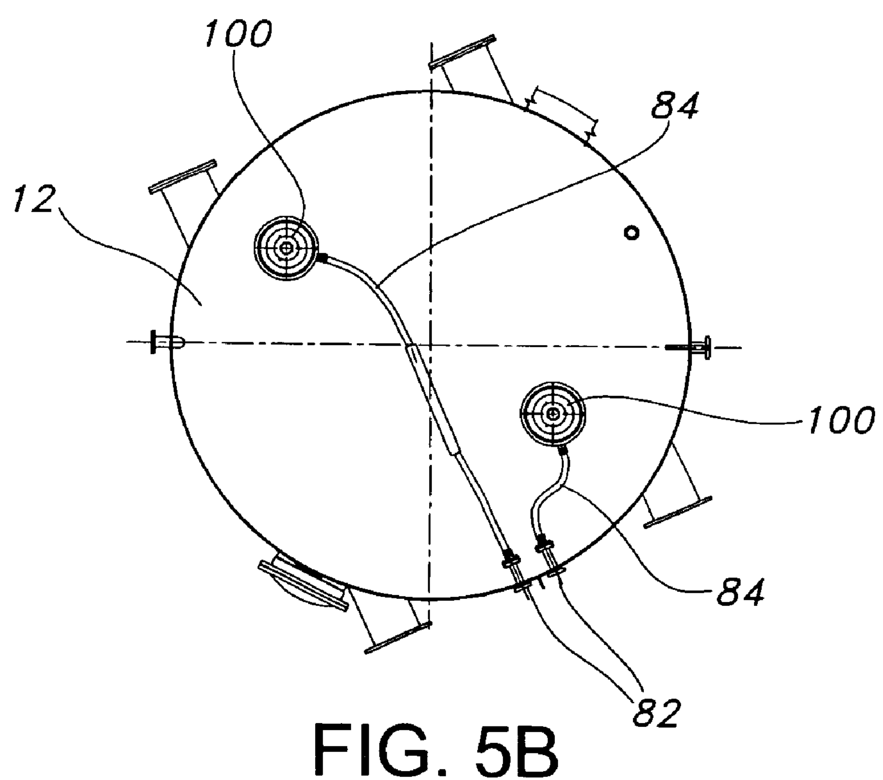
FIG. 5B is a plan view of the system illustrated in FIG. 5A.
Figure 5A:
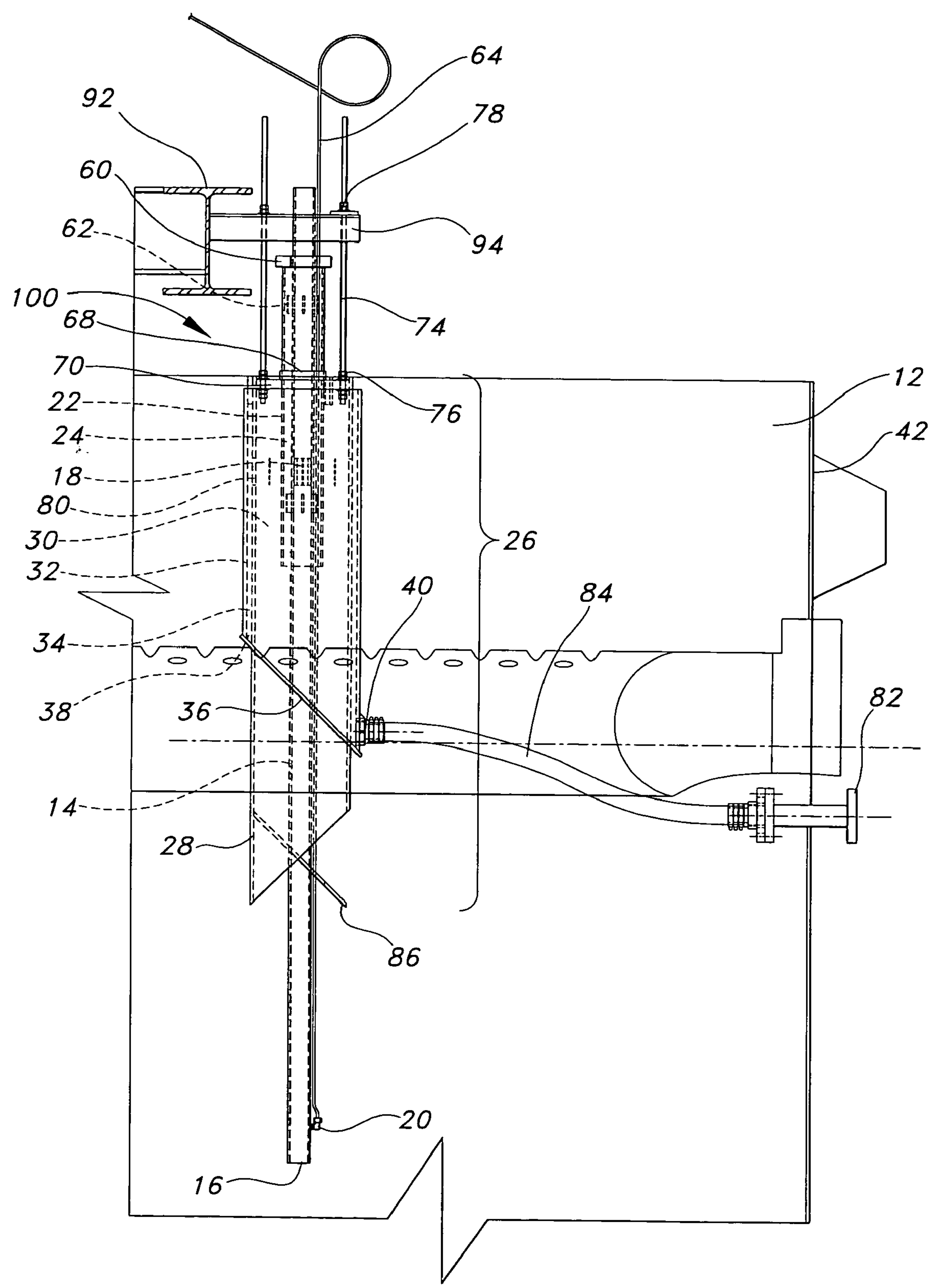
FIG. 5A is a partial side view of another embodiment of a system for separating biomass from media in a fluidized bed reactor, illustrating an excess biomass discharge positioned on the outer member illustrated in FIG. 4D in accordance with aspects of the present invention.

Referring specifically to FIGS. 5A and 5B, there is shown a system 100 for separating biomass from media in a fluidized bed reactor 12 containing an aqueous suspension of biomass and media. The configuration and operation of system 100 is virtually the same as those of system 10 described above with reference to FIGS. 1A-4C, with some notable differences.

Similar to system 10, system 100 is generally oriented along longitudinal axis A, and includes a lift 14 configured to extend within a reactor vessel is 42 of a fluidized bed reactor 12. Attached around the circumference of the lift 14 is a riser clamp 60 that rests on top of a shield 22 (disposed about the lift 14), thereby supporting the lift 14 in position with respect to the shield 22. The lift 14 includes spacers 62 located along its outer circumference to help center the lift 14 within the shield 22. The lift 14 has an inlet 16 for receiving aqueous suspension and outlets 18 spaced from the inlet 16 for delivering the aqueous suspension from the lift 14. A gas inlet 20 is positioned to feed gas into the lift 14 for urging the aqueous suspension toward the outlets 18 of the lift 14. The gas inlet 20 is fed by a gas line 64 which is supplied with gas at the gas port 66.

A first annular passageway 24 is defined between the shield 22 and the lift 14. The first annular passageway 24 is positioned to receive aqueous suspension from the outlets 18 of the lift 14. The shield 22 further includes a collar 68 around the circumference of the shield 22 that rests on a support plate 70, thereby supporting the shield 22 in position within the reactor vessel 42.

The system 100 further includes a biomass separator body 26 disposed about the shield 22. The support plate 70 located at the top portion of the biomass separator body 26 includes a round hole 72 in its center to accommodate the shield 22.

The biomass separator body 26 is suspended within the reactor vessel 42 by threaded rods 74 via fastener assemblies 76. The elevation of the biomass separator body 26 within the reactor vessel 42 is adjustable through manipulation of adjustment nuts 78.

The biomass separator body 26 includes an inner member 28 disposed about the shield 22 and a second annular passageway 30 is defined between the inner member 28 of the biomass separator body 26 and the shield 22. The second annular passageway 30 is positioned to receive aqueous suspension from the first annular passageway 24. The biomass separator 26 further includes an outer member 32, wherein a third annular passageway 34 is defined between the inner member 28 and the outer member 32. The inner member 28 includes apertures 80 through which the third annular passageway 24 receives aqueous suspension from the second annular passageway 30.

A barrier 36 extends between the inner member 28 and the outer member 32 at an end portion 38 of the third annular passageway 34. An excess biomass discharge 40 is in fluid communication with the third annular passageway 34. The barrier 36 of the biomass separator body 26 is configured to direct biomass from the third annular passageway 34 toward the excess biomass discharge 40. The excess biomass discharge 40 discharges excess biomass from the third annular passageway 34 through a vessel biomass discharge nozzle assembly 82 via a discharge hose 84.

A deflector 86 having a hole 88 to accommodate the lift 14 is positioned to deflect media exiting the inner member 28.

A notable difference from system 10 is that the general structure of the fluidized bed reactor 12 utilized in conjunction with system 100 does not include a dome or a cap assembly. A beam 92 provides structural support for the system 100 via a support platform 94. The system illustrated in FIGS. 5A and 5B is an anoxic bioreactor system.

As explained above, the biomass separator body 26 is suspended within the reactor vessel 42 by threaded rods 74. More specifically, the support plate 70 located at the top portion of the biomass separator body 26 is fixedly secured to the threaded rods 74 via fastener assemblies 76. Each threaded rod 74 extends upwardly from the support plate 70 of the biomass separator body 26 through the support platform 94 and is moveably secured via a respective adjustment nut 78. The elevation of the biomass separator body 26 within the reactor vessel 42 is adjustable through manipulation of the adjustment nuts 78, as explained above with reference to system 10 in conjunction with FIG. 1A.

Another notable difference from system 10 is the elevation and orientation of the excess biomass discharge 40 of system 100. More specifically, the end portion 38 of the outer member 32 is at a higher elevation, as illustrated in FIG. 5A. The barrier 36 extends between the inner member 28 and the outer member 32 at the end portion 38 of the third annular passageway 34. The excess biomass discharge 40 is positioned on the outer member 32, and is in fluid communication with the third annular passageway 34. As explained above with reference to system 10 in conjunction with FIG. 1A, the barrier 36 of the biomass separator body 26 is configured to direct biomass from the third annular passageway 34 toward the excess biomass discharge 40. More specifically, the barrier 36 is downwardly sloped to reduce buildup of biomass within the third annular passageway 34. The excess biomass discharge 40 discharges excess biomass from the third annular passageway 34 through a vessel biomass discharge nozzle assembly 82 (located external to the reactor vessel 42) via a discharge hose 84.

While preferred embodiments of the invention have been shown and described herein, it will be understood that such embodiments are provided by way of example only. Numerous variations, changes and substitutions will occur to those skilled in the art without departing from the spirit of the invention. For example, FIGS. 1B and 5B illustrate two systems 10 and 100, respectively, within respective fluidized bed reactors 12. However, it is contemplated that a fluidized bed reactor system may include any number of systems (or one system) for separating biomass from media, depending upon various application scenarios. Another example is the elevation of the inlet 16 of the lift 14. Although it is illustrated in FIGS. 1B and 5B as toward the bottom of the FBR 12, it is contemplated that the elevation of the inlet 16 may be toward the top of the FBR 12, or any suitable point in between within the FBR 12. Yet another example is the various support mechanisms described above. More specifically, for example, although the lift 14 is supported within the shield 22 via the riser clamp 60 as described above, it is contemplated that the lift 14 may be supported within the shield via any other suitable support mechanism. Another example is the adjustability of the elevation of the biomass separator body 26 within the reactor vessel 42. Although such adjustment feature has been described above as utilizing adjustment nuts 78 in conjunction with respective threaded rods 74, it is contemplated that the elevation of the biomass separator body 26 may be adjustable within the reactor vessel 42 via any other suitable adjustment mechanism. Yet another example is the overall construction and assembly of the FBR 12, and more specifically the system 10, 100. Although the construction and assembly of the various components have been described above, it is contemplated that the system 10, 100 may be constructed and assembled in a variety of ways to achieve the desired improved system for removing accumulated biomass from a slurry of a fluidized-bed bioreactor to inhibit uncontrolled biomass growth and precipitate accumulation. Accordingly, it is intended that the appended claims cover all such variations as fall within the spirit and scope of the invention.

What is claimed:

1. A method for separating biomass from solid media in a fluidized bed reactor containing an aqueous suspension of biomass and solid media, said method comprising the steps of:

feeding gas into a lift extending within the fluidized bed reactor, thereby urging aqueous suspension from an inlet of the lift toward an outlet formed in the lift;

directing aqueous suspension through the outlet of the lift to a first annular passageway and;

flowing aqueous suspension from an outlet of the first annular passageway to a second annular passageway, thereby separating solid media from biomass;

redirecting aqueous suspension from the second annular passageway through at least one aperture to a third annular passageway, thereby separating additional solid media from biomass; and discharging biomass from the third annular passageway.

2. The method of claim 1, wherein said step of directing aqueous suspension from the outlet of the lift to a first annular passageway comprises maintaining a shield about the lift to define the first annular passageway.

3. The method of claim 1, wherein said step of flowing aqueous suspension from the first annular passageway to a second annular passageway comprises maintaining an inner member of a separator body about the shield to define the second annular passageway.

4. The method of claim 1, wherein said step of redirecting aqueous suspension from the second annular passageway to a third annular passageway comprises maintaining an outer member of a separator body about an inner member of the separator body to define the third annular passageway.

5. The method of claim 1, wherein said step of discharging biomass from the third annular passageway comprises discharging biomass from an interior of the third annular passageway.

6. The method of claim 1, wherein said step of discharging biomass from the third annular passageway comprises discharging biomass from an exterior of the third annular passageway.

7. The method of claim 1, further comprising the step of deflecting media exiting from the first or second annular passageway away from the inlet of the lift.

8. A method for separating biomass from media in a fluidized bed reactor containing an aqueous suspension of biomass and media, said method comprising the steps of:

feeding gas into a lift extending within the fluidized bed reactor, thereby urging aqueous suspension from an inlet of the lift toward an outlet formed in the lift;

directing aqueous suspension through the outlet of the lift to a first annular passageway and maintaining a shield about the lift to define the first annular passageway;

flowing aqueous suspension from the first annular passageway at a lower end of the shield to a second annular passageway, thereby separating media from biomass;

redirecting aqueous suspension from the second annular passageway through at least one aperture to a third annular passageway; and discharging biomass from the third annular passageway.

9. The method of claim 8, wherein said step of redirecting aqueous suspension from the second annular passageway to a third annular passageway comprises maintaining an outer member of a separator body about an inner member of the separator body to define the third annular passageway.

10. The method of claim 8, wherein said step of discharging biomass from the third annular passageway comprises discharging biomass from an interior of the third annular passageway.

11. The method of claim 8, wherein said step of discharging biomass from the third annular passageway comprises discharging biomass from an exterior of the third annular passageway.

12. A method for separating biomass from media in a fluidized bed reactor containing an aqueous suspension of biomass and media, said method comprising the steps of:

feeding gas into a lift extending within the fluidized bed reactor, thereby urging aqueous suspension from an inlet of the lift toward an outlet formed in the lift;

directing aqueous suspension through the outlet of the lift to a first annular passageway;

flowing aqueous suspension from an outlet the first annular passageway to a second annular passageway, thereby separating media from biomass, and maintaining an inner member of a separator body about the shield to define the second annular passageway;

redirecting aqueous suspension from the second annular passageway through the inner member to a third annular passageway; and discharging biomass from the third annular passageway.

13. The method of claim 12, wherein said step of redirecting aqueous suspension from the second annular passageway to a third annular passageway comprises maintaining an outer member of a separator body about an inner member of the separator body to define the third annular passageway.

14. The method of claim 12, wherein said step of discharging biomass from the third annular passageway comprises discharging biomass from an interior of the third annular passageway.

15. The method of claim 12, wherein said step of redirecting aqueous suspension from the second annular passageway to a third annular passageway comprises maintaining an outer member of a separator body about an inner member of the separator body to define the third annular passageway.

16. A method for separating biomass from media in a fluidized bed reactor containing an aqueous suspension of biomass and media, said method comprising the steps of:

feeding gas into a lift extending within the fluidized bed reactor, thereby urging aqueous suspension from an inlet of the lift toward an outlet formed in the lift;

directing aqueous suspension through the outlet of the lift to a first annular passageway;

flowing aqueous suspension from an outlet of the first annular passageway to an inlet of a second annular passageway, thereby separating media from biomass;

redirecting aqueous suspension from an outlet formed in the second annular passageway to a third annular passageway;

discharging biomass from the third annular passageway; and deflecting media exiting from the first or second annular passageway away from the inlet of the lift.

17. The method of claim 16, wherein said step of discharging biomass from the third annular passageway comprises discharging biomass from an interior of the third annular passageway.

18. The method of claim 16, wherein said step of discharging biomass from the third annular passageway comprises discharging biomass from an exterior of the third annular passageway.

19. The method of claim 16, further comprising the step of deflecting media exiting from the first or second annular passageway away from the inlet of the lift.

20. The method of claim 1, wherein said step of flowing aqueous suspension from the outlet of the first annular passageway to the second annular passageway comprises separating solid media from biomass such that separated solid media moves downwardly with respect to the biomass.

21. The method of claim 1, further comprising the step of adjusting the flow rate of the aqueous suspension from the second annular passageway to the third annular passageway.

22. The method of claim 21, wherein said step of adjusting the flow rate of the aqueous suspension from the second annular passageway to the third annular passageway comprises adjusting the elevation of the at least one aperture relative to the outlet of the first annular passageway.

* * * * *